US009168044B2

(12) United States Patent
Kirkham

(10) Patent No.: US 9,168,044 B2
(45) Date of Patent: Oct. 27, 2015

(54) MULTI-USE CLEAT

(76) Inventor: Jeffrey B. Kirkham, Sandy, UT (US)

(*) Notice: Subject to any disclaimer, the term of this patent is extended or adjusted under 35 U.S.C. 154(b) by 301 days.

(21) Appl. No.: 12/958,913

(22) Filed: Dec. 2, 2010

(65) Prior Publication Data

US 2011/0126382 A1 Jun. 2, 2011

Related U.S. Application Data

(63) Continuation-in-part of application No. 12/642,247, filed on Dec. 18, 2009.

(60) Provisional application No. 61/203,138, filed on Dec. 19, 2008.

(51) Int. Cl.
*A61B 17/00* (2006.01)
*A61F 5/48* (2006.01)
*A61B 17/132* (2006.01)
*F16G 11/04* (2006.01)
*F16G 11/14* (2006.01)

(52) U.S. Cl.
CPC ............ *A61B 17/1322* (2013.01); *F16G 11/04* (2013.01); *F16G 11/14* (2013.01); *Y10T 24/14* (2015.01); *Y10T 24/3989* (2015.01)

(58) Field of Classification Search
CPC ............ A61B 17/1327; A61B 17/132; A61B 17/0401; F16L 3/233; F16G 11/00
USPC ........ 24/16 R, 115 J, 336, 339; 114/218, 343, 114/364; D8/356; 606/203, 72, 103, 151, 606/232; 289/2–15; 602/16; 623/13.11, 623/13.13, 13.14
See application file for complete search history.

(56) References Cited

U.S. PATENT DOCUMENTS

| 1,583,343 | A |   | 5/1926  | Duerden              |
|-----------|---|---|---------|----------------------|
| 2,387,428 | A |   | 10/1945 | Brothers             |
| 2,497,596 | A | * | 2/1950  | Frieder et al. ........... 135/97 |
| 2,518,921 | A | * | 8/1950  | Middaugh ............ 606/203 |
| 2,968,117 | A | * | 1/1961  | Trombly .............. 446/27 |
| 3,409,014 | A | * | 11/1968 | Shannon .............. 606/148 |
| D218,515  | S |   | 8/1970  | Tomaiuolo            |
| D233,312  | S |   | 10/1974 | Lock                 |
| 3,910,280 | A | * | 10/1975 | Talonn ................ 606/203 |
| 4,149,540 | A | * | 4/1979  | Hasslinger ........... 606/203 |
| D289,373  | S |   | 4/1987  | Kimball              |
| 4,911,162 | A |   | 3/1990  | Wolff                |
| 4,964,419 | A | * | 10/1990 | Karriker ............... 128/879 |
| 5,282,825 | A |   | 2/1994  | Muck                 |

(Continued)

OTHER PUBLICATIONS

Author Unknown, Combat Application Tourniquet, retrieved 2008, www.combattourniquet.com/index.php.

(Continued)

*Primary Examiner* — Katherine Dowe
*Assistant Examiner* — Richard Louis
(74) *Attorney, Agent, or Firm* — Workman Nydegger

(57) ABSTRACT

A cord assembly including an elongate cord extending between a first end in the form of at least one loop and an opposite free second end and a cleat fixedly attached to the looped end of the elongate cord. The cleat includes at least two recesses for receiving and securing the second end of the elongate cord during use, for example, as a tourniquet or to secure some other item. In use, the free end is passed through the loop so that the cord extends around the limb or other item to which it is being applied, and then the free end of the cord is locked into the cleat using the recesses.

11 Claims, 13 Drawing Sheets

(56) References Cited

U.S. PATENT DOCUMENTS

| | | | |
|---|---|---|---|
| 5,314,456 A | 5/1994 | Cohen | |
| 5,665,109 A * | 9/1997 | Yoon | 606/232 |
| 5,990,402 A * | 11/1999 | Epstein | 84/422.3 |
| 6,149,618 A * | 11/2000 | Sato | 602/75 |
| 6,884,254 B2 * | 4/2005 | Brooks | 606/201 |
| 6,899,720 B1 * | 5/2005 | McMillan | 606/203 |
| 7,353,766 B1 * | 4/2008 | Wiese | 114/218 |
| 7,530,990 B2 * | 5/2009 | Perriello et al. | 606/232 |
| 8,661,624 B1 | 3/2014 | Bracewell | |
| 2003/0116984 A1 * | 6/2003 | Herman et al. | 294/82.12 |
| 2004/0084331 A1 * | 5/2004 | Roby et al. | 206/63.3 |
| 2005/0113866 A1 | 5/2005 | Heinz | |
| 2005/0273134 A1 | 12/2005 | Esposito | |
| 2006/0135969 A1 * | 6/2006 | Assia | 606/151 |
| 2007/0011850 A1 * | 1/2007 | Downing et al. | 24/16 R |
| 2007/0135841 A1 * | 6/2007 | Dreyfuss | 606/232 |
| 2007/0179531 A1 * | 8/2007 | Thornes | 606/232 |
| 2007/0299467 A1 | 12/2007 | Arias | |
| 2008/0119848 A1 * | 5/2008 | Shalaby et al. | 606/60 |
| 2009/0076546 A1 * | 3/2009 | Ashley et al. | 606/232 |
| 2009/0241297 A1 * | 10/2009 | Sorensen | 24/130 |
| 2010/0057120 A1 | 3/2010 | Kirkham | |
| 2010/0160957 A1 * | 6/2010 | Kirkham | 606/203 |
| 2011/0126382 A1 | 6/2011 | Kirkham | |

OTHER PUBLICATIONS

U.S. Appl. No. 12/642,247, Feb. 17, 2012, Office Action.

* cited by examiner

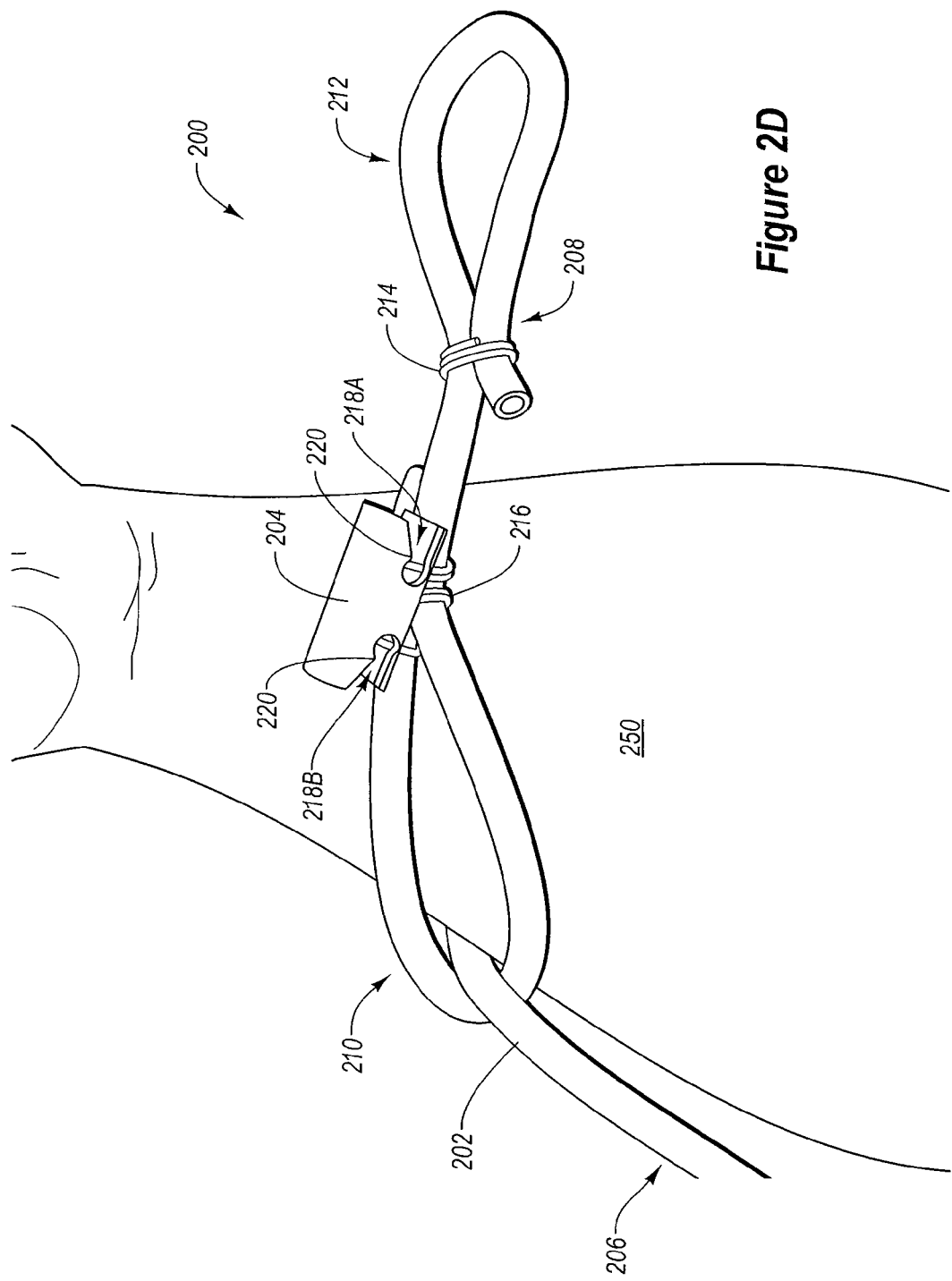

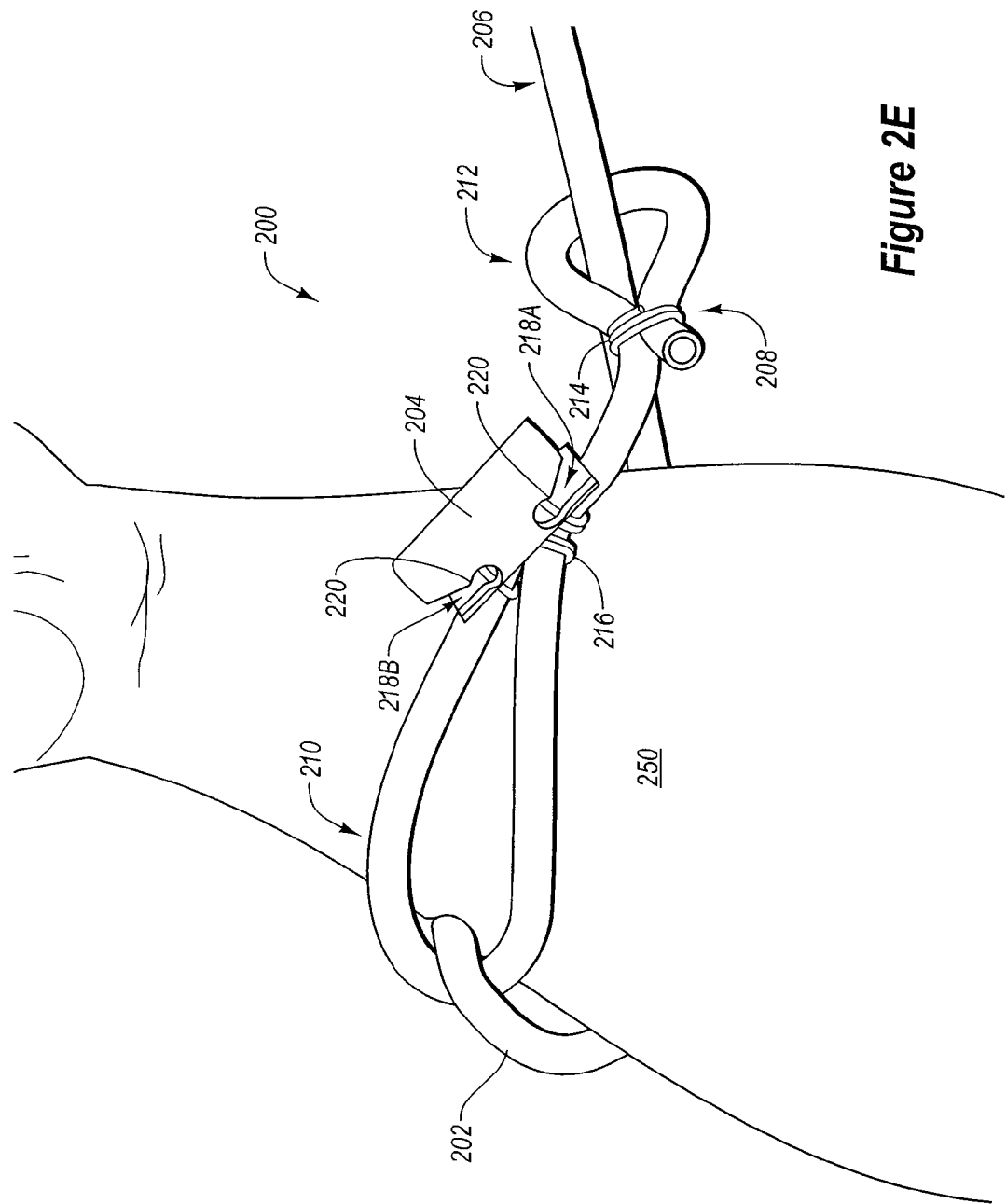

MULTI-USE CLEAT

CROSS-REFERENCE TO RELATED APPLICATIONS

This application is a continuation-in-part of U.S. patent application Ser. No. 12/642,247, filed Dec. 18, 2009, and titled "ONE-HANDED LOOP TOURNIQUET", which claims priority to U.S. Provisional Patent Application Ser. No. 61/203,138 filed Dec. 19, 2008, titled "ONE-HANDED LOOP TOURNIQUET", each of which are herein incorporated by reference in their entirety.

BACKGROUND OF THE INVENTION

The Relevant Technology

Various types of tourniquets have been used when necessary to stop the flow of blood through an injured arm or leg so as to prevent death of the injured through loss of blood. However, existing tourniquets are typically carried as a separate piece of gear and are often unwieldy and bulky, adding additional weight and bulk to the already substantial gear that a soldier or emergency services person must carry on his or her person. These difficulties can be compounded when an injured person attempts to fix the tourniquet on him or herself or another injured person. For example, even if the tourniquet is accessible, it may be very difficult to apply the tourniquet to one of the person's own arms with the use of only the remaining hand. Further, the environment within which the user finds himself during fixing of the tourniquet can be an issue (e.g., within a collapsing building or under enemy fire).

When medical personnel take blood from a patient, a rubber band or rubber tube is often used to restrict blood flow. However, the rubber band or rubber tubing is not intended to entirely stop blood flow. It is also difficult for medical personnel to fix the rubber band or rubber tube to the patient without the use both hands.

BRIEF SUMMARY

The present invention is directed to multi-use cleats, as well as methods for manufacturing and using multi-user cleats.

Embodiments of the invention include a multi-use cleat having defined openings configured to receive and to securely hold portions of a cord in a clasped and fixed position upon being placed into the cleat. One or more openings of a multi-use cleat can be configured with one or more teeth to assist in holding a cord in a clasped and fixed position. Openings of a multi-use cleat can also be arranged and configured to receive different types of cord, such as, for example, round cords, flat cords, etc. A multi-use cleat can be used to secure a cord for any number of different applications, including for use in tourniquets, maintaining tension in a line holding up a tent, etc.

These and other objects and features of the present invention will become more fully apparent from the following description, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIGS. 2D-2F illustrate the multiple loop tourniquet of FIG. 2A applied to a human extremity.

DETAILED DESCRIPTION

The present invention is directed to multi-use cleats, as well as their use and manufacture. Embodiments of the invention include a multi-use cleat having defined openings configured to receive and to securely hold portions of a cord in a clasped and fixed position upon being placed into the cleat. One or more openings of a multi-use cleat can be configured with one or more teeth to assist in holding a cord in a clasped and fixed position. Openings of a multi-use cleat can also be arranged and configured to receive different types of cord, such as, for example, round cords, flat cords, etc. A multi-use cleat can be used to secure a cord for any number of different applications, including for use in tourniquets, maintaining tension in a line holding up a tent, etc.

Some embodiments of the invention facilitate tourniquet use and application under a wide variety of different environmental conditions. More specifically, some embodiments of the invention provide quick and efficient tourniquet use and application under environmental conditions including one or more of: limited light conditions, self-application conditions, and when the person applying the tourniquet has use of only a single hand.

Single Loop Embodiments

Figure 1A:
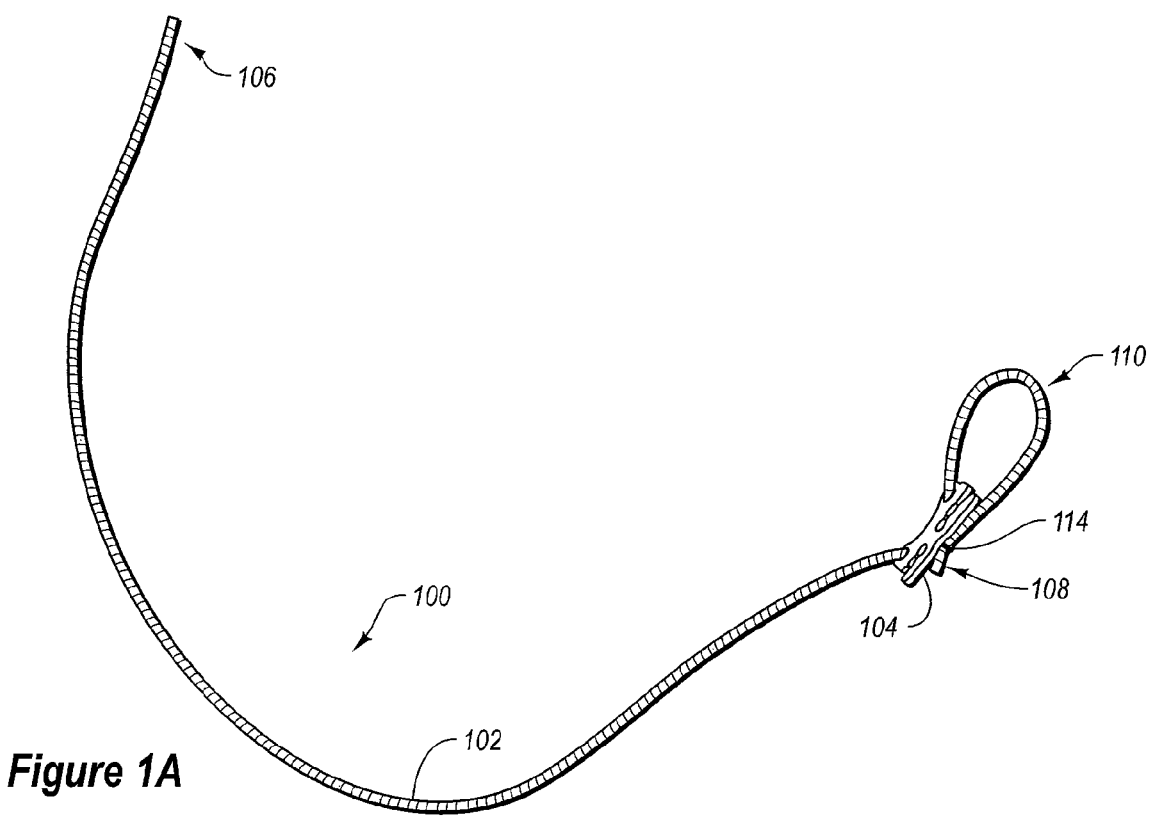
FIG. 1A illustrates a single loop tourniquet.
Figure 1B:
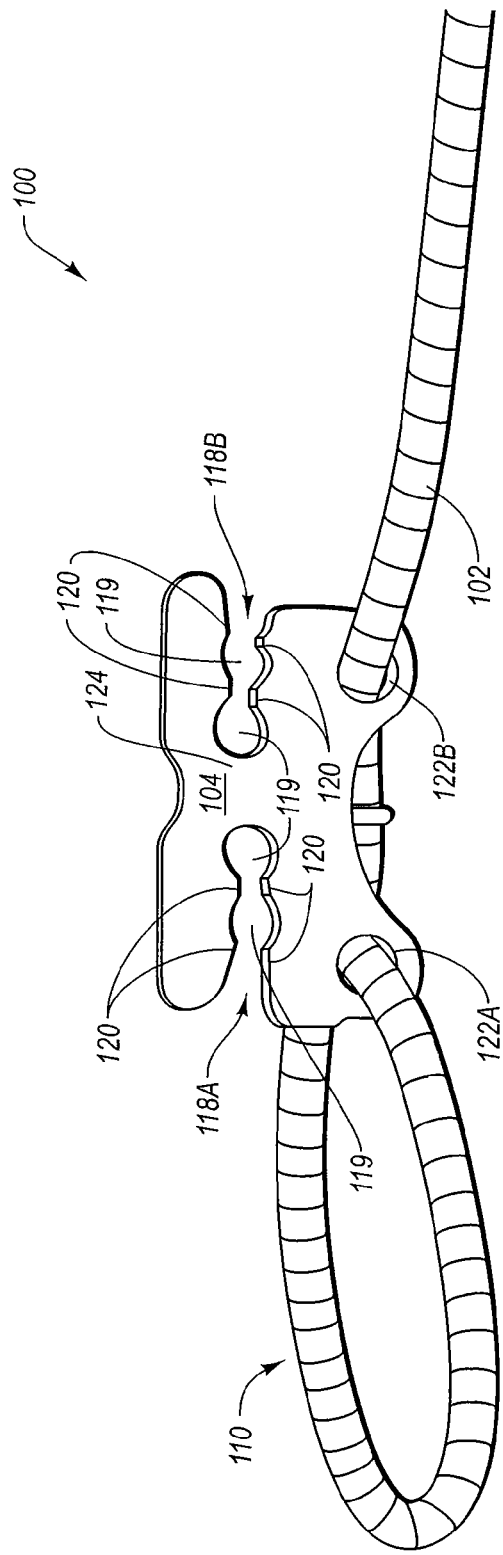
FIG. 1B illustrates another view of the single loop tourniquet of FIG. 1A.
Figure 1C:
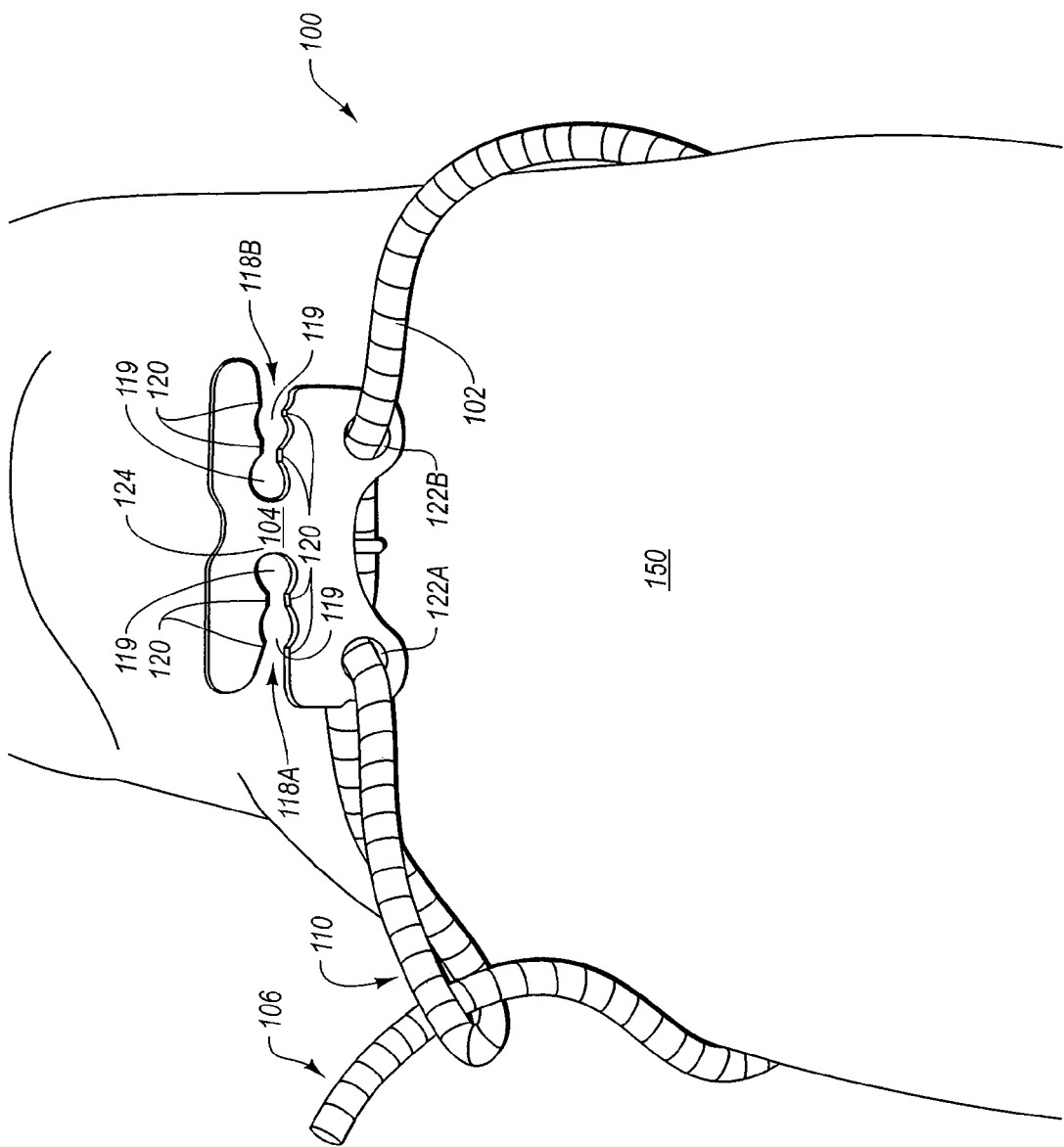
FIGS. 1C and 1D illustrate the single loop tourniquet of FIG. 1A applied to a human extremity.
Figure 1D:
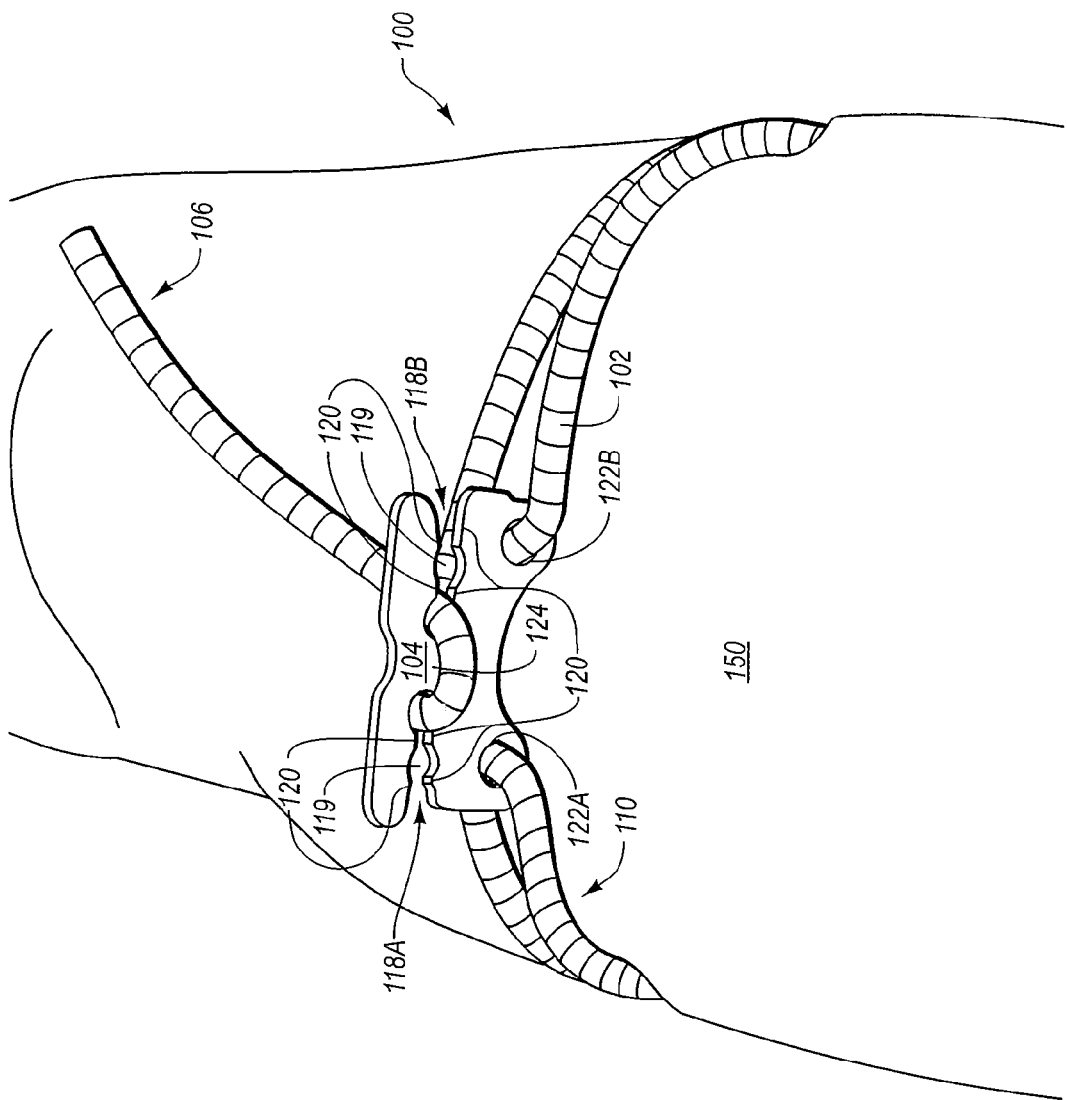

FIG. 1A depicts a tourniquet 100 incorporating aspects of the present invention including a loop 110. FIG. 1B depicts an additional view of single loop tourniquet 100. FIGS. 1C and 1D depict additional views of single loop tourniquet 100 in different stages of application to a human extremity (e.g., an arm or leg).

As depicted in FIG. 1A, tourniquet 100 includes cord 102, cleat 104, and clamp 114. Cord 102 includes end 106 and end 108. Generally, cord 102 can be wrapped around an extremity, such as, for example, an arm or leg (of a human or other animal), to constrict and/or compress venous and arterial circulation in the extremity. Pressure is applied circumferentially upon the skin and underlying tissues of the extremity. The pressure is transferred to the walls of underlying vessels, causing them to become occluded. Tourniquet 100 can be used for medical applications, such as, for example, to stem the flow of (potentially traumatic) bleeding, in military, search and rescue, and other environments.

Cord 102 can be constructed from any material, such as, for example, elastomeric materials, that permits cord 102 to be stretched when appropriate tension is applied. Stretching can help facilitate locking/clasping of cord 102 in place. In some embodiments, cord 102 is constructed from bungee cord materials. However, stretching may not be appropriate for all applications. Thus alternately, cord 102 can be constructed from materials that are not elastomeric and/or that do not stretch.

Cord 102 can be constructed in virtually any desired coloring pattern of a color or of a combination of colors. For example, cord 102 can be white with black helical stripes. Alternately, cord 102 can be high contrast yellow. In some embodiments (not shown), portions of cord 102 are constructed of a color having increased visibility in low light conditions. For example, some coloring patterns can include white, red, orange or yellow pigment that is applied to end 106 and/or end 108, while remaining portions of cord 102 are colored with a different pigment. Alternately, all of cord 102 can be colored with the same pigment.

The length of the cord 102 can vary to accommodate any need and preference. In one embodiment, the cord 102 is configured to have a length of at least one foot. In other embodiments, the cord 102 has a length of greater than two feet.

The cross-sectional area of cord 102 can also vary to accommodate any need and preference. Generally, the cross-sectional area (e.g., diameter) of cord 102 is sufficient to prevent cord 102 from cutting and permanently damaging the tissue around which the tourniquet 100 applied. Any elastomeric properties of the cord material of cord 102 can also help prevent tissue damage. For example, cord 102 can stretch and give way when tension is applied to cord 102, while still enabling the cord 102 to be sufficiently tightened into place.

The cross-sectional shape of cord 102 can also vary to accommodate any need and preference. Although cord 102 is depicted as having a round cross section, virtually any cross-section shape can be used. For example, a "flat" cord can be used in which the cross-section of cord 102 is generally rectangular (and potentially square). A cord with a rectangular cross-section can provide for a larger surface area of contact against the tissue where the tourniquet is applied. Increased contact surface area can result in less discomfort and/or pinching of the skin around an area where tourniquet 100 is applied.

Clamp 114 is used to attach end 108 back to cord 102, forming loop 110. Clamp 114 can be used during manufacture of tourniquet 100 to fix or form loop 110 into a desired size and placement on cord 102. Clamp 114 can be a plastic or metal clamp. Other attachment mechanisms for forming or fixing loop 110 can also be used. For example, loop 110 can be formed through weaving or sewing processes in which portions of cord 102 are sewn or woven together with natural, synthetic, and/or even metallic fibers and other similar elements. Adhesives, knots, pins, buckles, and other attachment means can also be used to attach portions of the cord 102 together in such a way to form loop 110. In other embodiments (not shown), a loop is selectably adjustable. For example, buckles or clamps can be used to attach portions of cord 102 together so as to adjust the size of loop 110 into a releasably fixed state.

As depicted in FIG. 1A, the configuration of loop 110 assists in holding cleat 104 in an appropriate orientation (e.g., an upright position) relative to the surface of an object, such as, for examiner, an arm or leg, when applying tourniquet 100 to the object.

Turning now to FIG. 1B, FIG. 1B depicts another view of tourniquet 100. FIG. 1B depicts a closer view of the configuration of cleat 104. As depicted, cleat 104 is configured with cord holes 122A and 122B. Cord holes 122A and 122B allow cord 102 to pass through the cleat 104 so as to flexibly hold the cleat 104 in a desired placement. Cord 102 is enabled to freely slide through the cord holes 122A and 122B to some extent. However, cleat 104 can remain held within a predetermined range of movement due to cleat 104 being attached to loop 110. As a result, cleat 104 is prevented from being entirely removed from cord 102. To facilitate such a configuration, loop 110 is formed (fixedly or releasably with a suitable attachment means) after the cord 102 is passed through at least one of the cord holes 122A and 122B.

With more specific reference to cleat 104, cleat 104 also includes recesses 118A and 118B. Each of recesses 118A and 118B include recessed areas 119 (e.g., pockets) and teeth 120. Recessed areas 119 and teeth 120 are configured to facilitate multiple points of engagement for cord 102 within each of recesses 118A and 118B. These multiple points of engagement permit cord 102 to be wrapped around stem 124 multiple times.

When cord 102 is wrapped around the stem 124 multiple times (not shown), recessed areas 119 and teeth 120 engage cord 102 at a plurality of points on the cord 102. For example, recessed areas 119 and teeth 120 engage cord 102 at each point in which the cord 102 passes through either of recesses 118A and 118B and around the stem 124. Referring briefly to FIG. 1D, FIG. 1D depicts end 106 wrapped around stem 124 a single time (with two points of passage). However, cord 102 can be wrapped around stem 124 an additional time, in which case four portions of the cord 102 would be engaged within the teeth 120, rather than two.

To increase the precision of the cleat 104 and teeth 120 in engaging cord 102, teeth 120 can be formed with a water jet process that cuts teeth into the cleat 104 with precise tolerances. Cleat 104 can also be formed from injection molding, stamping, forging or casting processes, depending on the material of the cleat 104. In some embodiments the cleat 104 is formed of a plastic. In other embodiments, cleat 104 is formed partially or entirely out of metal. Two part molding processes can also be used to configure the cleat 104 out of different materials, such as, for example, to expose one material within the recess portions 118A and 118B and to manufacture the rest of the cleat 104 out of another material.

Cleat 104 can be constructed in virtually any desired coloring pattern of a color or of a combination of colors. For example, the cleat 104 can be colored with a fluorescing pigment or another coloring pattern that facilitates identification in low light conditions. In some embodiments, the color of cleat 104 is selected to contrast with the color pattern of cord 102 so that the different components of tourniquet 100 are more easily distinguished from one another.

Turning now to FIG. 1C, FIG. 1C depicts an earlier stage of applying tourniquet 100 to a surface. As depicted, tourniquet 100 is laid on a leg 150 with the cleat 104 side up. Next, end 106 is fed through the loop 110. Turning to FIG. 1D, after end 106 is pulled through the loop 110, end 106 is then pulled in the opposite direction around the underside of the leg 150 and up to cleat 104. End 106 is then pulled through recess 118A, wrapped around stem 124, and pulled through recess 118B. Recess areas 119 and teeth 120 in recesses 118A and 118B hold cord 102 securely in place.

Although not shown, cord 102 can also be wrapped around the leg 150 again, one or more times, and tightened in place around the cleat 104 (after each time it is wrapped around the leg 150, or only once after all of the wraps are completed, or any desired number of times).

Multiple Loop Embodiments

Figure 2A:
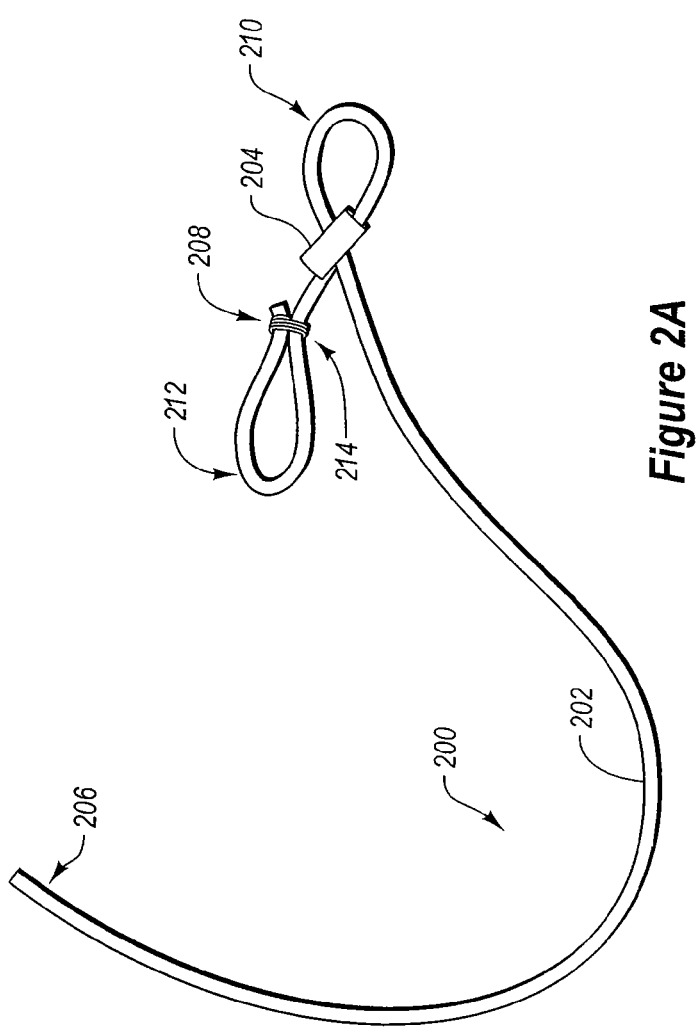
FIG. 2A illustrates a multiple loop tourniquet.
Figure 2B:
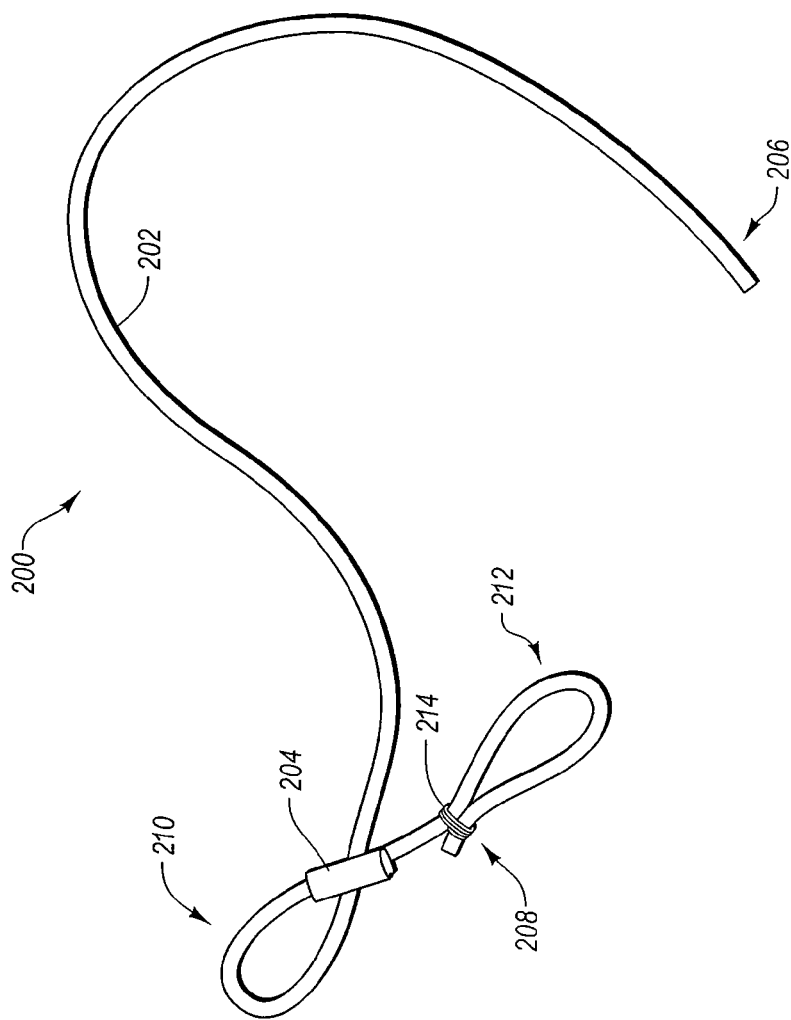
FIGS. 2B and 2C illustrate other views of the multiple loop tourniquet of FIG. 2A.
Figure 2C:
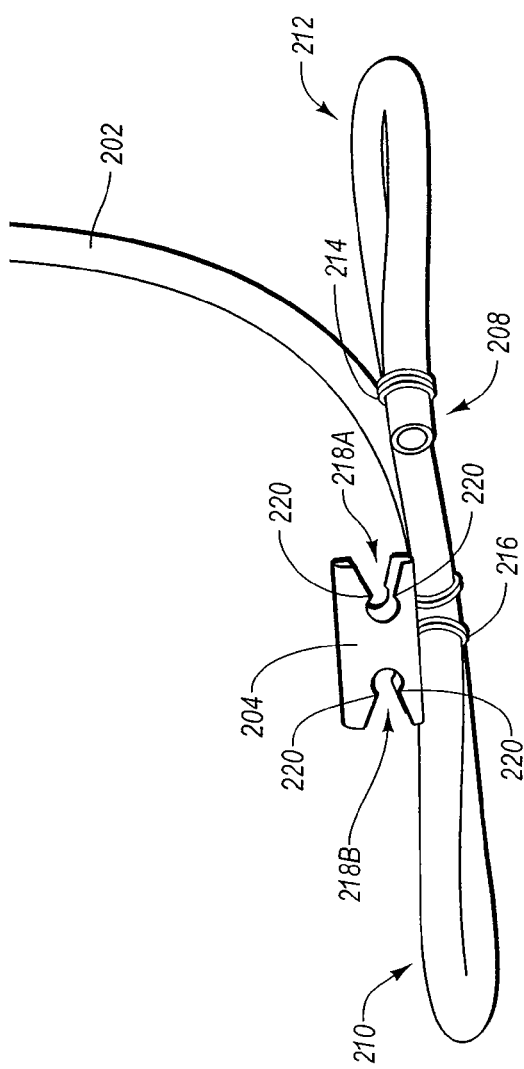
Figure 2F:
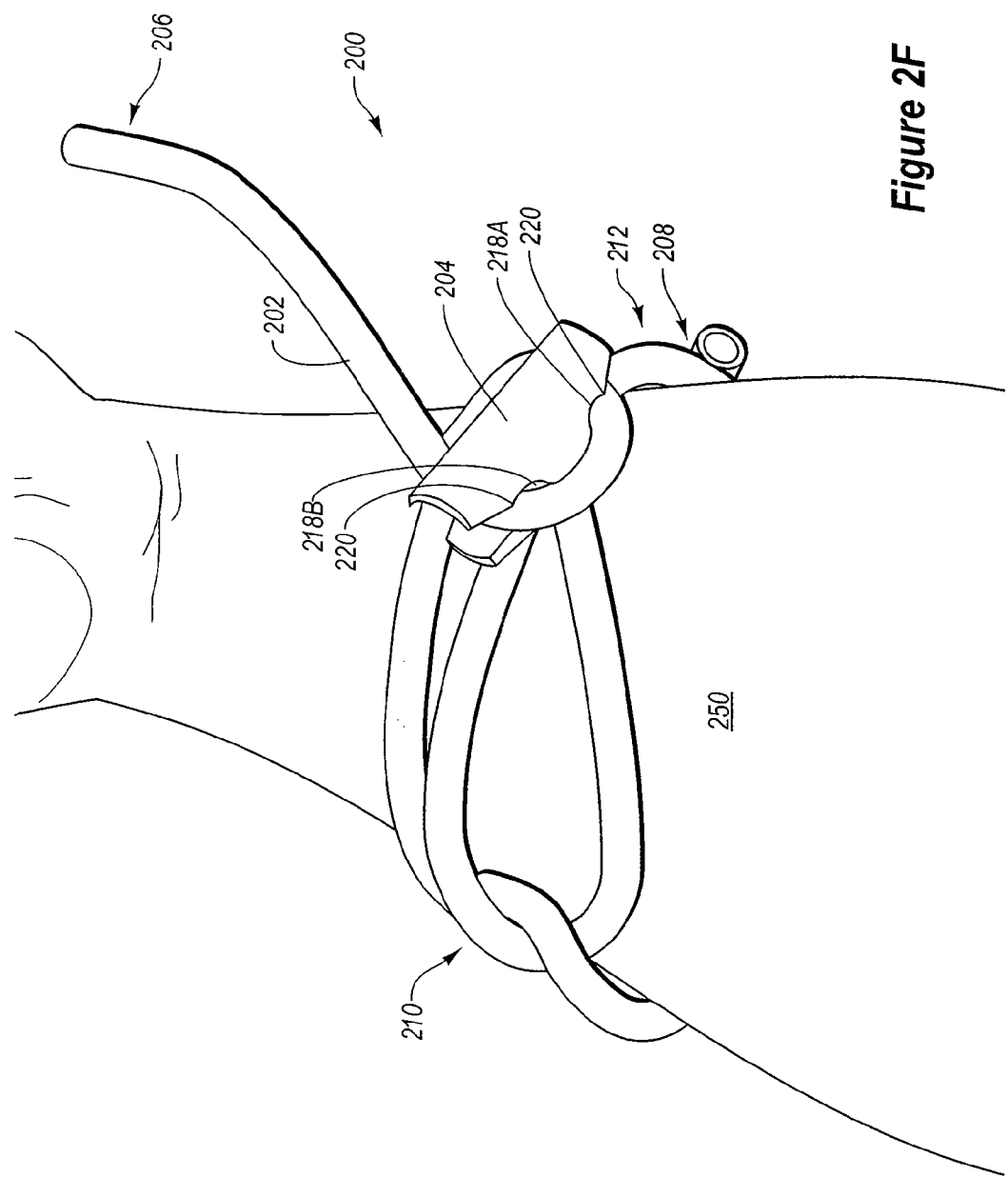

FIG. 2A depicts another tourniquet 200 incorporating aspects of the present invention including loops 210 and 212. FIGS. 2B and 2C depict additional views of multi-loop tourniquet 200. FIGS. 2D—2F depict additional views of multiple loop tourniquet 200 in different stages of application to a human extremity (e.g., an arm or leg).

As depicted in FIG. 2A, tourniquet 200 includes cord 202, cleat 204, and clamp 214. Cord 202 includes end 206 and end 208. Similar to cord 102, cord 202 can be wrapped around an extremity, such as, for example, an arm or leg (of a human or other animal), to constrict and/or compress venous and arterial circulation in the extremity. Tourniquet 200 can also be used for medical applications, such as, for example, to stem the flow of (potentially traumatic) bleeding, in military, search and rescue, and other environments.

The construction of cord 202, including materials, length, color, cross-sectional shape, and cross-sectional area, can be varied similar to the construction of cord 102, to accommodate any need or preference.

As depicted in FIG. 2A, tourniquet 200 includes loops 210 and 212. Cleat 204 is used to attach portions of cord 202 to one another, forming loop 210. Clamp 214 is used to attach end 208 back to cord 202, forming loop 212. Cleat 204 and clamp 214 can be constructed using processes and materials similar to those used to construct clamp 114.

Cleat 204 and/or clamp 214 can be used during manufacture of tourniquet 200 to fix or form loops 210 and/or 212 into a desired size and placement on cord 102. Other attachment mechanisms for forming or fixing loops can also be used. For example, loops can be formed through weaving or sewing processes in which portions of cord 202 are sewn or woven together with natural, synthetic, and/or even metallic fibers and other similar elements. Adhesives, knots, pins, buckles, and other attachment means can also be used to attach portions of the cord 202 together in such a way to form loops. In other embodiments (not shown), a loop is selectably adjustable. For example, buckles or clamps can be used to attach portions of cord 202 together so as to adjust the size of loops 210 and/or 212 into a releasably fixed state.

FIG. 2B depicts an alternate view of tourniquet 200.

Turning to FIG. 2C, cleat 204 can be fixed to cord 202, for example, with any of the attachment means described above, including metallic wires 216 or other elements. As depicted, cleat 204 includes slotted recesses 218A and 218B that are configured in size and shape to receive and securely engage the cord 202. Slotted recesses 218A and 218B can include locking means, such as teeth 220, or other formations that pinch, lock onto, or otherwise engage cord 202 when cord 202 is placed into slotted recesses 218A and 218B. Other locking means, such as pins, latches and even Velcro type straps can also be used to lock cord 102 into place within slotted recesses 218A and 218B.

Turning to FIG. 2D, FIG. 2D depicts an early stage of applying tourniquet 200 to a surface. As depicted in FIG. 2D, tourniquet 200 is laid on arm 250 with the cleat 204 side up (positioned above the cord 202). Loop 212 is shown to be extending away from arm 250, with loop 110 resting on arm 250. The shape of loop 212 helps to stabilize tourniquet 200 in position while end 206 is pulled through the additional loop 210. The ability of tourniquet 200 to rest stably, with cleat 204 being held above the cord 202, is also visible in FIG. 2A. This stability is advantageous for ensuring that the cleat 204 is accessible during application.

Turning to FIG. 2E, after end 206 of the cord 202 is pulled through loop 210, end 206 is wrapped under arm 250 (or other object the tourniquet 100 is being applied to) and fed through the first loop 212. Turning to FIG. 2F, end 206 is then pulled back under the arm/object 250 (from the direction it came), and locked into position by the cleat 204. The tightness of tourniquet 200 can be adjusted by pulling end 106 to a desired degree of tightness (prior to locking cord 202 into position within the cleat 104).

Cord 202 is held in a locked position within the cleat 204 after passing cord 202 through both of the recesses 218A and 218B. It will be appreciated, however, that it is not always necessary to pull cord 202 through both recesses 218A and 218B prior to locking cord 202 in a fixed position. For example, it may be sufficient to pull cord 202 through one of recesses 218A and 218B when the cord 202 is configured with knots, anchors or other structures (not shown, but which can be included) that further engage with the cleat 204 and that are positioned on end 106. It will also be appreciated that the cleat 204 can be configured with different configurations of teeth 220 and recesses 218, to enable the cord 202 to pass into and engage with the cleat 204 in a different manner.

In one alternative embodiment, a cleat includes a plurality of small teeth that extend entirely along a recess that is longer in length than the recesses shown in FIGS. 2A-2F.

In other embodiments, recesses 218A and 218B are rotated 90 degrees about the cylindrical axis passing through cleat 204 and such that cord 202 can be passed through cleat 204, in alignment with the axis and pulled up through one of recesses 218A and 218B into a locked position.

While recesses 218A and 218B are shown to have a fixed shape and a substantially rounded interior surface at their ends, it will be appreciated that cleat 204 can also be configured with an angled entry that extends all the way to the interior end of the recesses 218A and/or 218B, with teeth structures 220 lining the interior of the recesses 218A and/or 218B that are configured to securely engage and hold onto cord 202. Other shapes and sizes of the recesses 218A and/or 218B can also be employed. For example, the entry to recesses 218A and/or 218B can be outwardly flared, so as to more easily facilitate entry of cord 202.

Further configurations of cleat 204 include forming cleat 204 out of any suitable plastic and/or metal material. In some embodiments, cleat 204 is formed from existing piping material (plastic (PVC-type piping) or metal piping) that is cut to size and then manufactured to have the desired recesses 218A and/or 218B. The recesses 218A and/or 218B can be formed through stamping, melting or any desired cutting and/or sanding processes.

The foregoing examples refer expressly to tourniquet 200 having two loops, 210 and 212. However, tourniquets having three or more loops are also contemplated. Any additional loops, which are positioned between loops 210 and 212 beneficially minimizes the distance that has to be traversed from loop 112 in order to apply the tourniquet 200, particularly when the tourniquet 100 is being applied around larger objects, such as legs. In these embodiments, the user can selectively choose which of the additional loops to feed end 106 through. It is also possible to have multiple passes go through loop 112 as well as one or more of the additional loops, (as well as to wrap the cord 102 around the entire object before or after feeding the cord 102 through the loop(s)), so as to increase the surface area of cord 202 applied to the object. Increasing the surface area applies additional pressure while minimizing potential tissue damage that could result from wrapping cord 202 around an object a single time.

In embodiments in which the cord 102 is wrapped around the object multiple times (entirely, or partially with the use of the loops), the length of the tourniquet cord 102 can be manufactured with an increased length (e.g., three or more feet).

Multi-Use Cleat

Figure 3:
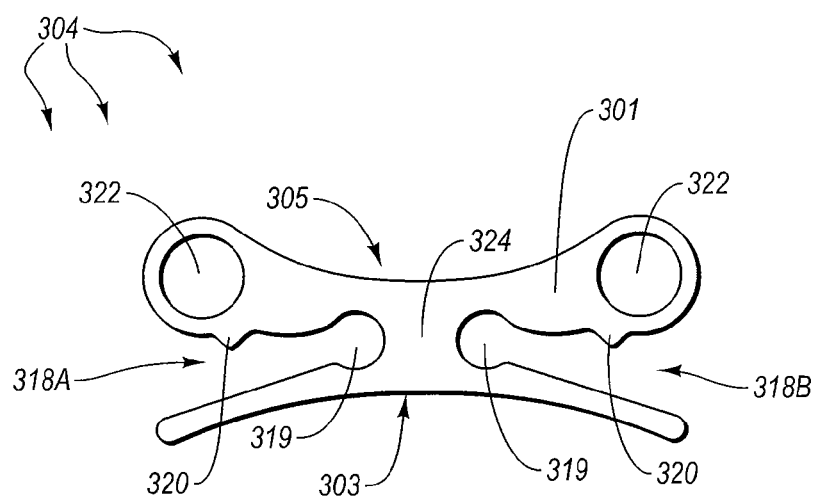
FIG. 3 illustrates a multi-use cleat

FIG. 3 illustrates cleat 304 that can be used to secure a cord, such as, for example, with single loop and multiple loop tourniquets (e.g., tourniquet 100 and/or tourniquet 200), to secure a line on a tent, etc. Cleat 304 includes a body 301 including a base end 303 and a securing end 305. Cleat 304 includes slotted recesses 318A and 318B, which divide the base end 303 from the securing end 305. Base end 303 and securing end 305 are connected by stem 324 between recesses 318. Recesses 318A and 318B are sized to receive and securely engage a cord (e.g., cord 102, 202, etc.). Slotted recesses 318A and 318B can include locking means, such as the illustrated teeth 220, or other formations that pinch, lock onto, or otherwise engage a cord when it is placed into the slotted recesses 318A and 318B. Cleat 304 can be formed out of any suitable plastic and/or metal material.

Cleat 304 further includes cord holes 322 that allow a cord to pass through the cleat 304 and to flexibly hold the cleat 304 in a desired placement relative to a limb or other item to which a cord being applied. Thus, cleat 304 may also be used for other clasping purposes, apart from application of a tourniquet. In such instances (e.g., for use in securing a rope of a tarp or other camping/outdoor equipment) the presence of holes 322 provides a similar "hold in place" benefit so that base end 303 is held against a desired surface. While the cord is enabled to freely slide through cord holes 322, cleat 304 is still held within a predetermined range of movement due to the fact that part of the cord is passed through one of cord holes 322. If one end of the cord includes a loop, this may prevent cleat 304 from being entirely removed from the looped end of the cord.

Although cleat 304 is shown including a single tooth 320 within each recess 318A and 318B, it will be understood that additional teeth may be present (e.g., similar to the cleat 104). Each recess 318A and 318B is depicted as including a rounded recess 319 at its end, adjacent stem 324. Circular recess 319 may be advantageously sized to accommodate the diameter of a round cord. Because of the inclusion of recesses 319 and teeth 320 (which are spaced apart so as to be near the opposite end of recesses 318A and 318B relative to rounded portion 319) a cord may be wrapped around stem 324 multiple times. When a cord is wrapped around stem 324 multiple times, teeth 320 and recessed areas 319 engage the cord at a plurality of points to hold the cord in place between rounded recess 319 and tooth 320.

Figure 4:
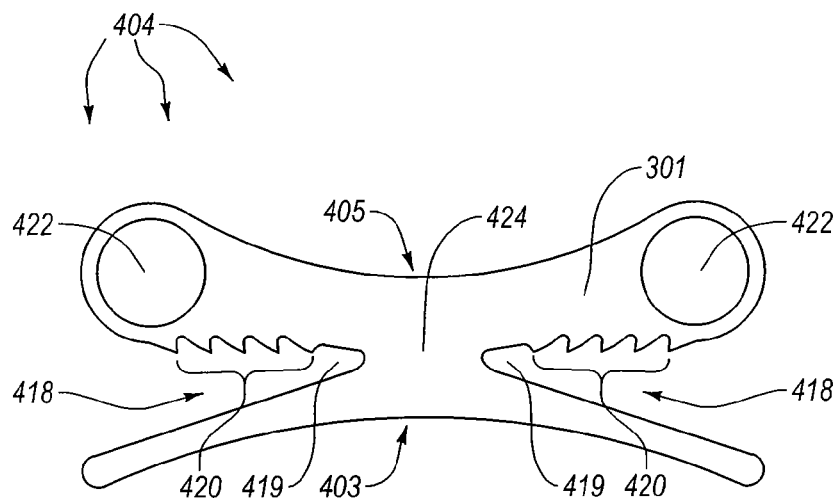
FIG. 4 illustrates another multi-use cleat

Turning to FIG. 4, another cleat 404 is depicted. Cleat 404 includes a body 401 including a base end 403 and a securing end 405. Cleat 404 includes slotted recesses 418A and 418B, which divide the base end 403 from the securing end 405. Base end 403 and securing end 405 are connected by stem 424 between recesses 418. Recesses 418A and 418B are sized to receive and securely engage a cord (e.g., cord 102, 202, etc.). Each of slotted recesses 418A and 418B include a plurality of teeth 420 configured pinch, lock onto, or otherwise engage a cord when it is placed into the slotted recesses 418A and 418B. Cleat 404 can be formed out of any suitable plastic and/or metal material.

Cleat 404 further includes cord holes 422 that allow a cord to pass through the cleat 404 and to flexibly hold the cleat 404 in a desired placement relative to a limb to or other item to which it is being applied. Thus, cleat 404 may also be used for other clasping purposes, apart from application of a tourniquet. In such instances (e.g., for use in securing a rope of a tarp or other camping/outdoor equipment) the presence of holes 422 provides a similar "hold in place" benefit so that base end 403 is held against a desired surface. While the cord is enabled to freely slide through cord holes 422, cleat 404 is still held within a predetermined range of movement due to the fact that part of the cord is passed through one of cord holes 422. If one end of the cord includes a loop, this may prevent cleat 404 from being entirely removed from the looped end of the cord.

Although cleat 404 is shown including with a particular arrangement of teeth 420 within each recess 418A and 418B, it will be understood that additional teeth may be configured and arrangement in any number of different ways. For example, the size, length, and spacing between each of teeth 420 can be varied to suit different applications. Each recess 418A and 418B is depicted as including a recess 419 at its end, adjacent stem 424. Recess 419 may be advantageously sized to accommodate a specified type of cord. Because of the inclusion of recesses 419 and teeth 420 a cord may be wrapped around stem 424 multiple times. When a cord is wrapped around stem 424 multiple times, teeth 420 and recessed areas 419 engage the cord at a plurality of points to hold the cord in place between rounded recess 419 and teeth 420.

Figure 5:
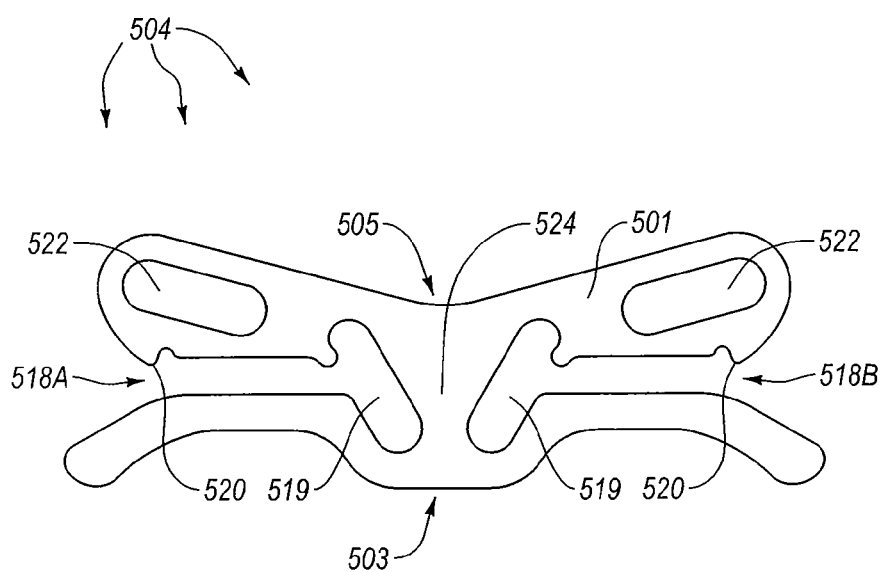
FIG. 5 illustrates a further multi-use cleat

Turning to FIG. 5, another cleat 504 is depicted. Cleat 504 includes a body 501 including a base end 503 and a securing end 505. Cleat 504 includes slotted recesses 518A and 518B, which divide the base end 503 from the securing end 505. Base end 503 and securing end 505 are connected by stem 524 between recesses 518. Recesses 518A and 5418B are sized to receive and securely engage a cord, such as, for example, a flat cord. Each of slotted recesses 518A and 518B include a tooth 520 configured pinch, lock onto, or otherwise engage a cord when it is placed into the slotted recesses 518A and 518B. Cleat 504 can be formed out of any suitable plastic and/or metal material.

Cleat 504 further includes cord holes 522 that allow a cord to pass through the cleat 504 and to flexibly hold the cleat 504 in a desired placement relative to a limb to or other item to which it is being applied. Thus, cleat 504 may also be used for other clasping purposes, apart from application of a tourniquet. In such instances (e.g., for use in securing a rope of a tarp or other camping/outdoor equipment) the presence of holes 522 provides a similar "hold in place" benefit so that base end 503 is held against a desired surface. While the cord is enabled to freely slide through cord holes 522, cleat 504 is still held within a predetermined range of movement due to the fact that part of the cord is passed through one of cord holes 522. If one end of the cord includes a loop, this may prevent cleat 504 from being entirely removed from the looped end of the cord.

Although cleat 504 is shown including a single tooth 520 within each recess 518A and 518B, it will be understood that additional teeth may be present (e.g., similar to the cleat 104 or 404). Each recess 518A and 518B is depicted as including a recess 519 at its end, adjacent stem 524. Recess 519 may be advantageously sized to accommodate the diameter of a flat cord. Because of the inclusion of recesses 519 and teeth 520 (which are spaced apart so as to be near the opposite end of recesses 518A and 518B relative to recesses 519) a cord may be wrapped around stem 524 multiple times. When a cord is wrapped around stem 524 multiple times, teeth 520 and recessed areas 519 engage the cord at a plurality of points to hold the cord in place between rounded recess 519 and tooth 520.

As mentioned above, a cleat (e.g., cleat 104, 204, 304, 404, and 504) may be used for a variety of different applications. Cleats can be used to secure a cord for essentially any purpose, for example, securing a camping tarp cord or securing a cord for other camping, outdoor, or other activity.

Accordingly, embodiments of the invention include cord assemblies where a cord is wrapped around an arm, leg, or other object and secured within a multi-use cleat. A cord can be constructed from material that permits the cord to stretch when appropriate tension is applied. Stretching can facilitate locking locking/clasping a cord in place within a multi-user cleat.

Figure 6:
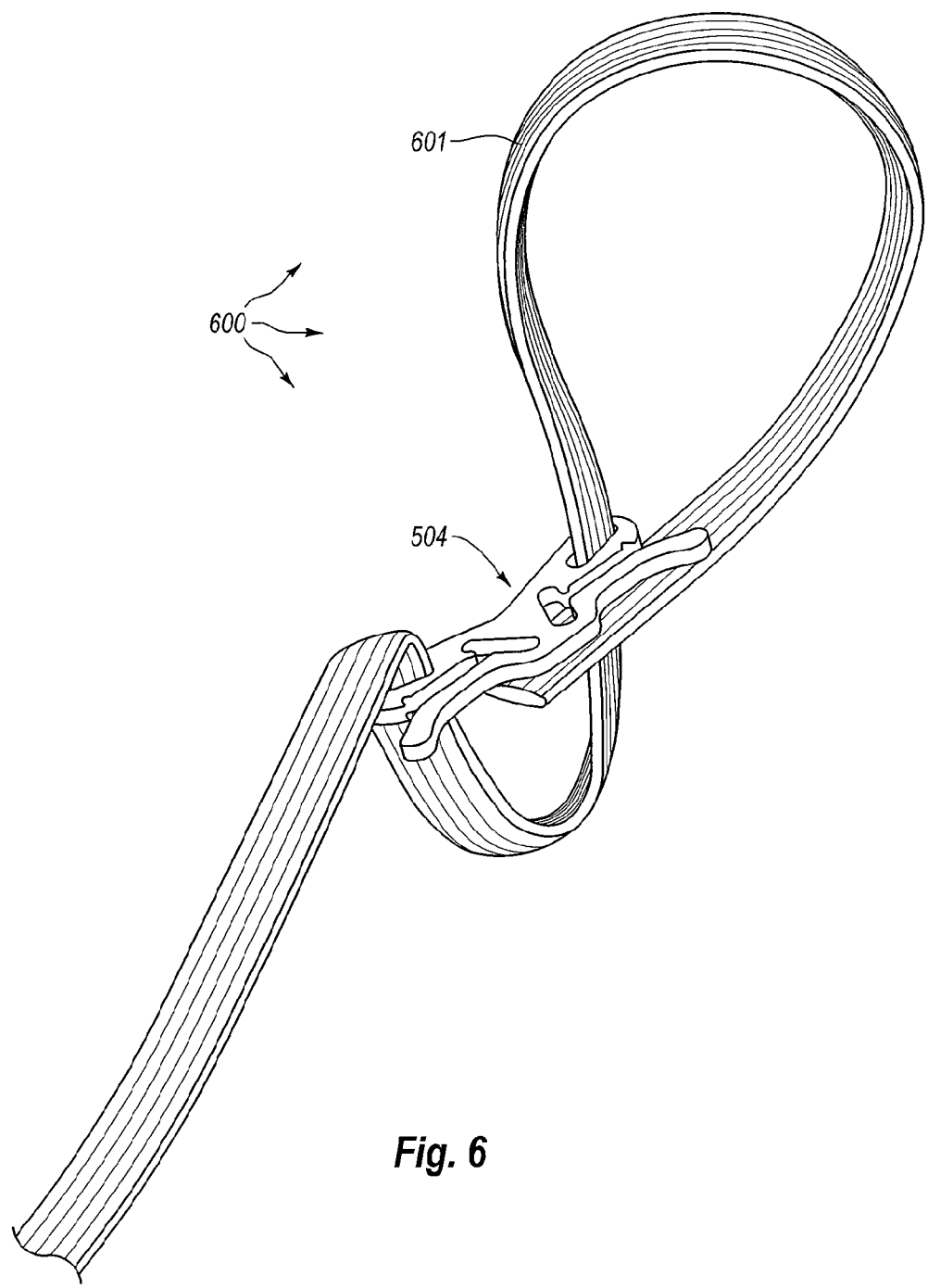
FIG. 6 illustrates a cord assembly with the multi-use cleat of FIG. 5.

FIG. 6 illustrates a cord assembly 600. As depicted, cord assembly 600 includes flat cord 601 being secured to cleat 504.

In view of the foregoing, it will be appreciated that the present invention provides many different cord applications having one or more fixed loops. Various advantages of the invention should be apparent from the foregoing disclosure, including the increased utility of being able to secure a cord with a single hand (due to the configuration of the loops and cleats).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A tourniquet assembly, comprising:
a cleat that includes:
a body with a base end and a securing end;
a first recess formed within a first side of the body dividing the base end from the securing end of the body on the first side of the body, the first recess extending between an outward opening and a closed inward end including a first enlarged recess at the inward end of the first recess;
a second recess formed within a second side of the body, opposite the first side of the body, dividing the base end from the securing end of the body on the second side of the body, the second recess extending between an outward opening and a closed inward end including a second enlarged recess at the inward end of the second recess;
a central stem directly connecting the base end of the body to the securing end of the body, the central stem being disposed between and separating the first and second enlarged recesses; and
the securing end of the body including a first hole formed into the first side of the body and a second hole formed into the second side of the body; and
an elongate cord, the cord extending between a first end and an opposite end, the first end being formed into a first fixed loop by an attachment mechanism that is composed of a different material than the elongate cord and which fixedly and non-adjustably attaches the first end of the cord directly to a different portion of the cord, wherein a portion of the first fixed loop passes directly through the first hole and such that the first end of the cord is secured to the securing end of the cleat body by having a portion of the first end of the cord that forms the first fixed loop pass directly through the first hole, and wherein the opposite end of the elongate cord passes directly through the second hole to form a second loop, the second loop being disposed between the first hole and the second hole.

2. The tourniquet assembly as recited in claim 1, wherein the elongate cord is an elongate flat cord, being defined by a flat cross-sectional shaped area.

3. The tourniquet assembly as recited in claim 2, wherein the elongate flat cord comprises an elastic material.

4. The tourniquet assembly as recited in claim 3, wherein the elongate flat cord is at least 1 foot in length.

5. The tourniquet assembly as recited in claim 3, wherein the elongate flat cord has a length greater than 2 feet.

6. The tourniquet assembly as recited in claim 1, wherein the attachment mechanism that fixedly and non-adjustably attaches the first end of the cord directly to a different portion of the cord comprises a metal clamp.

7. The tourniquet assembly as recited in claim 1, wherein the recesses of the cleat further comprise locking means for lockingly engaging the elongate cord when the elongate cord is placed in the recesses.

8. The tourniquet assembly as recited in claim 1, wherein the first and second recesses of the cleat are outwardly flared at their outward openings to facilitate insertion of the elongate cord during use.

9. The tourniquet assembly recited in claim 1, wherein the first hole and the second hole are oblong-shaped cord holes.

10. The tourniquet as recited in claim 1, wherein the central stem is tapered and narrower near the base end than near the securing end.

11. The tourniquet assembly as recited in claim 1, wherein the attachment mechanism that fixedly and non-adjustably attaches the first end of the cord directly to a different portion of the cord comprises a plastic clamp.

* * * * *